United States Patent
Dalko et al.

(10) Patent No.: US 6,930,192 B2
(45) Date of Patent: Aug. 16, 2005

(54) METHODS FOR PREPARING 7ALPHA-HYDROXY-DEHYDROEPIANDROSTERONE

(75) Inventors: Maria Dalko, Gif sur Yvette (FR); Alexandre Cavezza, Tremblay-en-France (FR); Valerie Wohlfromm, Sevran (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/467,172
(22) PCT Filed: Feb. 7, 2002
(86) PCT No.: PCT/FR02/00477
§ 371 (c)(1),
(2), (4) Date: Jan. 15, 2004
(87) PCT Pub. No.: WO02/064614
PCT Pub. Date: Aug. 22, 2002

(65) Prior Publication Data
US 2004/0133020 A1 Jul. 8, 2004

(30) Foreign Application Priority Data
Feb. 14, 2001 (FR) .............................. 01 01998

(51) Int. Cl.⁷ .............................. C07J 1/00; C07J 75/00
(52) U.S. Cl. ........................................ 552/615
(58) Field of Search ......................... 552/615

(56) References Cited

U.S. PATENT DOCUMENTS

| | | | |
|---|---|---|---|
| 5,277,907 A | 1/1994 | Loria | |
| 5,461,042 A | 10/1995 | Loria | |
| 5,693,809 A | 12/1997 | Durette et al. | |
| 2003/0054021 A1 | 3/2003 | Dalko et al. | |

FOREIGN PATENT DOCUMENTS

| | | |
|---|---|---|
| FR | 2 793 491 | 11/2000 |
| WO | 92 03925 | 3/1992 |
| WO | 93 20696 | 10/1993 |
| WO | 94 23722 | 10/1994 |
| WO | 98 50409 | 11/1998 |
| WO | WO 03/035023 A1 | 5/2003 |

OTHER PUBLICATIONS

Starka, Collection of Czechoslovakian Chemical Communications, vol. 26, p. 2452–2456 (1961).*
P. Marwah et al.: "Steroidal allylic fluorination using diethylaminosulfur trifluoride: A convenient method for the synthesis of 3beta–acetoxy–7alpha– and 7beta–fluoroandrost–5–en–17–one" Steroids: Structure, Function, and Regulation, vol. 61, No. 8, pp. 453–460, Aug. 1, 1996.
Jar Salvador et al.: "Copper catalysed allylic oxidation of DELTA–steroids by t–butyl hydroperoxide" Tetrahedron Letters, vol. 38, No. 1, pp. 119–122 Jan. 6, 1997.
V. Pouzar et al.: "Synthesis of (19E)–3beta, 7alpha–dihydroxy–17oxoandrost–5–en–19–al 19-(0–carboxymethyl)oxime, a new hapten for 7alpha–hydroxydehydroepiandrosterone(3beta,7alpha–dihydroxyandrost–5–en–17–one)—7alpha–hydroxylation of dehydroepiandrosterone and pregnenolone by rat brain microsomes" Steroids: Structure, Function, and Regulation, vol. 63, No. 9, pp. 454–458, Sep. 1, 1998.

* cited by examiner

Primary Examiner—Bernard Dentz
(74) Attorney, Agent, or Firm—Oblon, Spivak, McClelland, Maier & Neustadt, P.C.

(57) ABSTRACT

The invention relates to new processes for preparing 7alpha-hydroxy-dehydroepiandrosterone of formula (1):

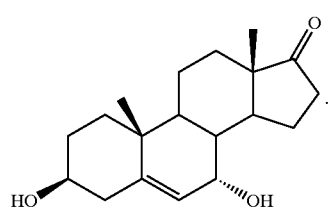

(1)

57 Claims, No Drawings

METHODS FOR PREPARING 7ALPHA-HYDROXY-DEHYDROEPIANDROSTERONE

This application is a 371 of PCT/FR02/00477 filed Feb. 07, 2002.

The invention relates to new processes for preparing 7alpha-hydroxy-dehydroepiandrosterone of formula (1):

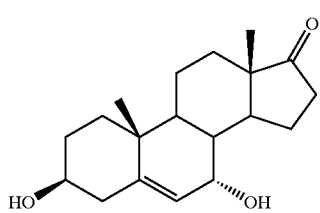

7alpha-Hydroxy-dehydroepiandrosterone (7α-OH-DHEA) is a derivative well known in the scientific literature; the following documents may be cited in particular:

FR-A1-2 771 105;
WO-A1-94/03176 and WO-A1-92/03925.

Each of the aforementioned documents reports a synthesis process for 7α-OH-DHEA. FR-A1-2 771 105 describes a process for preparing 7α-OH-DHEA in one step from dehydroepiandrosterone (DHEA), using a fungus: *Fusarium moniliforme*. This bioconversion process allows the direct transformation of DHEA into its 7-alpha-hydroxylated derivative with a yield of 79%.

This process allows the preparation of 7α-hydroxy-DHEA in a single step, but uses *Fusarium moniliforme*, which is a microscopic phytopathogenic fungus. This fungus attacks maize and sorghum (see in particular a document published on the internet at the following site: http://pested.unl.edu/catmans/fum.skp/fumchp8.htm). In addition, *Fusarium moniliforme* secretes oncogenic toxins which may prove highly dangerous to humans (see in particular a document published on the internet at the following site: http://www.hsafety.unc.edu/Manuals/LabManual/app7a.htm).

WO-A1-94/03176 and WO-A1-92/03925 describe a 4-step chemical process for preparing 7α-OH-DHEA from 3-O-acetyl-DHEA.

The first step of this process makes it possible to obtain 3-O-acetyl-7-bromo-DHEA from 3-O-acetyl-DHEA (commercial starting product) by treatment with a brominating agent. The mixture of 3-O-acetyl-7-bromo-DHEA isomers obtained is unstable and must be used quickly in the remainder of the process.

In a second step the racemic mixture of 7α-bromo and 7β-bromo isomers is equilibrated to give the 7α-bromo isomer (the more thermodynamically stable isomer) in majority form.

Following equilibration, the 3-O-acetyl-7-bromo-DHEA, treated with a mixture of glacial acetic acid and silver acetate, makes it possible to obtain 3-O-acetyl-7α-O-acetyl-DHEA.

3-O-Acetyl-7α-O-acetyl-DHEA, treated with sodium carbonate (Na₂CO₃) in a mixture consisting of water and methanol, gives 7α-OH-DHEA, which is subsequently purified by crystallization.

This 4-step synthesis process has the prime disadvantage of necessitating a non-stereoselective bromination step (second step), which leads to unstable brominated intermediates. Furthermore, the process necessitates an equilibration step, permitting the thermodynamic isomer (7α-bromo-3-O-acetyl-DHEA) to be obtained predominantly. The equilibration step as described in WO-A1-94/03176 and WO-A1-92/03925 is ambiguous, since the relative proportion of the isomers 7α- and 7β-bromo-3-O-acetyl-DHEA obtained after equilibration is not specified.

It should also be noted that the process described does not report the yield obtained and does not specify the optical purity of the resultant 7α-OH-DHEA, this compound being documented solely by its melting point following recrystallization (192–193° C.).

Furthermore, the deacetalization conditions which are reported in the prior art do not allow satisfactory production of 7α-OH-DHEA from 3-O-acetyl-7α-OH-DHEA.

These conditions consist
either in a conventional method of saponification, using sodium hydroxide in an aqueous medium,
or in a method described in WO-A1-94/03176 and WO-A1-92/03925, which involves a reaction of double deacetalization of 3-O-acetyl-7-O-acetyl-DHEA by treatment with sodium carbonate in a mixture consisting of water and methanol.

These methods, applied to the reaction of deacetalization of 3-O-acetyl-7-O-acetyl-DHEA or of 3-O-acetyl-7α-OH-DHEA, lead to mixtures of products in which 7α-OH-DHEA occurs predominantly. This is because the reaction conditions used are not adapted and lead to the formation of decomposition products including in particular those obtained from the dehydration of the alcohol in position 7 of 3-O-acetyl-7α-OH-DHEA. There is therefore understandable interest in implementing processes which allow the preparation of 7α-OH-DHEA simply and rapidly, with industrially acceptable yields, with a diastereoselectivity which does not require a step of equilibration or of removal of the minority diastereoisomer (7β-OH), the processes having the advantage, moreover, of not involving phytopathogenic and/or oncogenic microorganisms.

Furthermore, the processes according to the present invention also have the advantage of including a deacetalization reaction which allows 7α-OH-DHEA to be obtained from 3-O-acetyl-7α-OH-DHEA under satisfactory conditions without the formation of decomposition products.

This is the aim of the present invention, whose objects include providing novel synthesis processes for DHEA.

The present invention provides a process for preparing 7α-OH-DHEA of formula (1) from 3-O-acetyl-7α-OH-DHEA of formula (4) according to a step (iii) consisting in a transesterification reaction using an alkali metal alkoxide in the corresponding alcohol.

The transesterification reaction which is used in the process of the invention consists essentially in a) dissolving 3-O-acetyl-7α-OH-DHEA in an alcoholic solvent selected from ethanol, methanol and tert-butanol, preferably methanol;
b) adding between 1 and 3 equivalents, preferably between 1.5 and 3 equivalents, advantageously 1 equivalent of an alkali metal alkoxide, the alkoxide being selected preferably from the ethoxide, the tert-butoxide and the methoxide, advantageously the methoxide, and the alkali metal being selected preferably from lithium, sodium and potassium, advantageously sodium;
c) stirring the reaction mixture for a period of between 0.5 and 12 h, preferably between 1 h and 5 h, advantageously for 2 h;
d) evaporating the reaction solvent and diluting the mixture with water before extracting it with a solvent selected preferably from dichloromethane, ethyl acetate, chloroform and diethyl ether, advantageously dichloromethane;
e) drying the organic phase and then evaporating it to dryness;

f) optionally purifying the residue, for example by chromatography.

Advantageously the invention relates to a process for preparing 7α-OH-DHEA of formula (1) from 3-O-acetyl-7-oxo-DHEA of formula (3) comprising step (iii) as defined above, characterized in that step (iii) is preceded by a step (ii) comprising a regioselective and diastereoselective reduction of 3-O-acetyl-7-oxo-DHEA using L-Selectride® as reducing agent.

According to one preferred embodiment of the invention, the reduction of the enone of 3-O-acetyl-7-oxo-DHEA of formula (3) can be accomplished regio-selectively and diastereoselectively, without prior protection of the carbonyl in position 17, by using as reducing agent L-Selectride® or lithium tri-sec-butyl-borohydride ($LiB[CH(CH_3)C_2H_5]_3H$) in accordance with a method described in *Steroids*, 1998, 63, 454–458, which has been modified.

This method consists essentially in
a) preparing a solution of 3-O-acetyl-7-oxo-DHEA in an anhydrous organic polar solvent selected from tetrahydrofuran (THF), benzene and diethyl ether, preferably THF;
b) cooling the solution to a temperature of between −90 and −10° C., preferably between −80 and −60° C., advantageously to −78° C.;
c) adding under an inert atmosphere between 0.9 and 1.1 equivalents of L-Selectride®, preferably between 0.95 and 1.05 and, advantageously, 1 equivalent;
d) stirring the solution at a temperature of between −90 and −10° C., preferably between −80 and −60° C., advantageously at −78° C. for a period of between 1 and 10 h, preferably for 5 h;
e) taking the temperature of the reaction mixture to between −10 and 10° C., preferably to 0° C.;
f) adding aqueous sodium hydroxide (NaOH) solution, preferably at a concentration of between 1 and 10 M, advantageously 6 M, followed by aqueous hydrogen peroxide ($H_2O_2$) solution, preferably at 30 to 50%, advantageously at 30%, and stirring at ambient temperature;
g) diluting the reaction mixture in an organic polar solvent selected from diethyl ether, ethyl acetate, chloroform and dichloromethane, preferably diethyl ether;
h) washing the mixture a number of times by aqueous acidic washing, preferably with at least one aqueous 5% citric acid solution, then washing with at least one aqueous basic solution, preferably with saturated potassium bicarbonate ($KHCO_3$) solution, then washing with at least one aqueous neutral solution;
i) drying the organic phase and then evaporating it to dryness;
j) optionally purifying the residue, for example by chromatography.

Advantageously the invention relates to a process for preparing 7α-OH-DHEA of formula (1) from 3-O-acetyl-DHEA of formula (2) which comprises steps (iii) and (ii) as described above, characterized in that step (ii) is preceded by a step (i) consisting in a reaction of oxidation in the allyl position of 3-O-acetyl-DHEA.

FIG. 1 illustrates this 3-step synthesis process for 7α-OH-DHEA in accordance with the invention.

According to the invention a first preferred embodiment of the oxidation reaction in the allyl position of 3-O-acetyl-DHEA of formula (2) is carried out according to a method described in *Tetrahedron Letters*, 1997, 38, 119–122, which has been modified. This document describes a method of allylic oxidation by a peroxide in the presence of a copper salt catalyst on steroid frameworks.

This method consists essentially in
a) dissolving 3-O-acetyl-DHEA in an organic solvent or a mixture of organic solvents, selected preferably from acetonitrile, cyclohexane, benzene, methanol, ethanol and tert-butanol, advantageously acetonitrile;
b) adding under an inert atmosphere between 0.005 and 0.1 equivalent of copper, preferably 0.01 equivalent, preferably in the form of a copper salt, selected for example from copper iodide (CuI), copper bromide (CuBr), copper chloride (CuCl) and copper(II) chloride ($CuCl_2$), advantageously CuI;
c) cooling the reaction mixture at a temperature of between −10 and 10° C., advantageously between 5 and 10° C.;
d) adding dropwise between 5 and 10 equivalents, preferably 6 equivalents, of organic or inorganic peroxide, preferably organic peroxide, selected for example from alkyl hydroperoxide, advantageously t-butyl hydroperoxide (t-BuOOH);
e) allowing the temperature of the reaction mixture to rise to ambient temperature and stirring it for a period of between 0.5 and 4 h, preferably 2 h;
f) heating the mixture at a temperature of between 40 and 80° C., preferably between 50 and 70° C., advantageously at 50° C., for a period of between 4 and 72 h, preferably between 16 and 24 h, advantageously for 20 h;
g) cooling the reaction mixture and adding it to an aqueous alkaline solution, preferably 10% sodium bicarbonate ($NaHCO_3$) solution;
h) extracting the aqueous phase with an organic solvent, selected for example from diethyl ether, ethyl acetate, chloroform and dichloromethane, preferably diethyl ether, then washing the organic phases with an aqueous alkaline solution, preferably saturated aqueous $NaHCO_3$ solution, and optionally with saturated aqueous sodium chloride (NaCl) solution;
i) drying the organic phases and evaporating them to dryness under vacuum;
j) optionally purifying the residue in accordance with customary methods.

According to the invention a second preferred embodiment of the oxidation reaction in the allyl position of 3-O-acetyl-DHEA of formula (2) is carried out according to a method described in WO 92/03925 and WO 94/03176, which has been modified. These documents describe a method of allyl oxidation of 3-O-acetyl-DHEA by a mixture of acid anhydride, acetic acid and sodium acetate in the presence of chromium trioxide ($CrO_3$).

This method consists essentially in
a) preparing a mixture consisting of 3-O-acetyl-DHEA; acid anhydride, in an amount of preferably between 3 and 20 equivalents, advantageously 11 equivalents; acetic acid, in an amount of preferably between 20 and 120 equivalents, advantageously 66 equivalents; and sodium acetate, in an amount of preferably between 1 and 5 equivalents, advantageously 3 equivalents;
b) subjecting the reaction mixture to stirring and heating it to a temperature of between 40 and 60° C., preferably between 56 and 58° C.;
c) adding between 1 and 10 equivalents of an oxide, preferably between 2 and 6 equivalents, advantageously 3.5 equivalents, the oxide being selectable from an oxide of chromium, of manganese, of selenium and of magnesium, and being preferably an oxide of chromium, advantageously chromium trioxide ($CrO_3$);
d) keeping the reaction mixture under stirring for a period of between 0.5 and 4 h, preferably for 1 h, at a temperature of between 40 and 60° C., preferably between 56 and 58° C.;

e) cooling the reaction mixture and adding it, with stirring, to a solution consisting of water and ice;
f) filtering off the resulting precipitate and then washing it a number of times with water;
g) drying the residue and optionally purifying it in accordance with customary methods; preferably the product is recrystallized.

According to the invention a third preferred embodiment of the oxidation reaction in the allyl position of 3-O-acetyl-DHEA of formula (2) is carried out by a method described in WO 98/50409, which has been modified. This document describes a method of allyl oxidation using an alkali metal periodate and an alkyl hydroperoxide.

This method consists essentially in
a) dissolving 3-O-acetyl-DHEA of formula (2) in an organic solvent or an organic solvent mixture, selected preferably from acetone, heptane, acetonitrile, tert-butanol, pyridine, petroleum ether, hexane, isooctane and cyclohexane, advantageously in a mixture consisting of acetone and heptane, very preferably in a 1/1 ratio;
b) adding between 10 and 15 equivalents of alkyl hydroperoxide, advantageously t-butyl hydroperoxide, preferably at 70% or 80% in water;
c) stirring the mixture at ambient temperature and adding between 1 and 5 equivalents, preferably 3 equivalents, of alkali metal periodate, advantageously sodium periodate ($NaIO_4$);
d) adding water in an amount sufficient to allow total solubilization of the periodate in the reaction mixture, advantageously between 10% and 50% by volume, preferably between 15% and 40% by volume, very preferably between 20% and 30% by volume;
e) adding between 1 and 5 equivalents, preferably 3 equivalents, of an organic base, preferably pyridine, or a weak inorganic base, selected preferably from alkali metal carbonates and bicarbonates, advantageously sodium bicarbonate;
f) stirring the solution for a period of between 8 and 48 h, preferably for 14 h, at ambient temperature;
g) diluting the reaction mixture with ethyl acetate, dichloromethane, chloroform or diethyl ether, preferably ethyl acetate;
h) washing the mixture a number of times with aqueous sodium sulphate solution and then with water;
i) drying the organic phase and then evaporating it to dryness;
j) optionally purifying the residue in accordance with customary methods, preferably by recrystallization.

According to the invention an inert atmosphere means argon or nitrogen and ambient temperature means a temperature between 15 and 25° C. The purification methods which can optionally be employed at the end of each of the steps of the processes in accordance with the invention are realized according to conventional methods used in organic synthesis.

As mentioned above, the reaction of reduction of 3-O-acetyl-DHEA by L-Selectride® is diastereo-selective: the diastereoisomer obtained selectively is 3-O-acetyl-7α-OH-DHEA. On the other hand the reaction of reduction of 3-O-acetyl-DHEA by L-Selectride® may give rise to a not insignificant amount of product reduced in positions 7 and 17. This secondary product can be easily removed, for example by chromatography, at this stage or after the transesterification reaction of step (iii).

However, in order to prevent the formation of the product reduced in positions 7 and 17 in step (ii), a process for preparing 7α-OH-DHEA in accordance with the present invention may further comprise additional steps of protection and then deprotection of the carbonyl in position 17 of the reacting species.

Thus the invention relates advantageously to a process for preparing 7alpha-hydroxy-dehydroepiandrosterone of formula (1) from 3-O-acetyl-dehydroepiandrosterone, comprising steps (i), (ii) and (iii) as described above, characterized in that it further comprises the following additional steps:
(iv) a reaction of protection of the carbonyl in position 17 of 3-O-acetyl-DHEA before step (i);
(v) a reaction of deprotection of the carbonyl in position 17 of the derivative obtained after step (ii), the said reaction of deprotection taking place before step (iii).

The protection of the carbonyl in position 17 of 3-O-acetyl-DHEA can be carried out in accordance with methods conventionally used in organic synthesis and well known to the person skilled in the art, such as, for example, those described in *Protective Groups in Organic Synthesis*, T. W. Greene, P. G. M. Wuts (Wiley Interscience).

According to the invention the carbonyl in position 17 of 3-O-acetyl-DHEA can be protected in cyclic or non-cyclic acetal form, in cyclic or non-cyclic dithioacetal form, in monothioacetal form, in O-substituted cyanohydrin form, in substituted hydrazone form, or in imine, enamine, imidazolidine or benzothiazole form. Advantageously the carbonyl in position 17 of 3-O-acetyl-DHEA can be protected in cyclic or non-cyclic acetal, cyclic or non-cyclic dithioacetal, imine, enamine or imidazolidine form.

According to the invention a first preferred embodiment of the protection of the carbonyl in position 17 of 3-O-acetyl-DHEA according to step (iv) can be carried out by protecting the carbonyl in position 17 in cyclic acetal form in accordance with a method described in *Synth. Comm.* 1995, 25, 395–404, which has been modified.

This method consists essentially in
a) preparing a solution consisting of 3-O-acetyl-DHEA of formula (2), a diol, preferably ethylene glycol, and an excess of desiccant, selected preferably from molecular sieve and ethyl orthoformate, preferably ethyl orthoformate, advantageously in a respective ratio of 1 mmol/3 ml/2 ml;
b) adding a catalytic amount of proton, the source thereof being advantageously para-toluenesulphonic acid or ion exchange resins;
c) stirring the mixture at a temperature of between 30 and 60° C., preferably at 40° C., for a period of between 1 and 8 h, preferably 3 h;
d) bringing the temperature of the reaction mixture to ambient temperature;
e) adding aqueous $NaHCO_3$ solution;
f) extracting the mixture with a solvent selected from dichloromethane, chloroform, ethyl acetate and diethyl ether, preferably with dichloromethane;
g) washing the organic phase, drying it and then evaporating it to dryness;
h) optionally purifying the residue in accordance with customary methods, preferably by chromatography on silica gel.

According to the invention a second preferred embodiment of the protection of the carbonyl in position 17 of 3-O-acetyl-DHEA according to step (iv) may be carried out by protecting the carbonyl in position 17 in cyclic acetal form in accordance with an azeotropic distillation method described in *Synth. Comm.* 1995, 25, 395–404, which has been modified.

This method consists essentially in
a) bringing to reflux a mixture consisting of 3-O-acetyl-DHEA of formula (2), ethylene glycol and para-toluenesulphonic acid (p-TsOH) in solution in benzene, preferably in a respective ratio of 1 mmol/5 ml/0.1 mmol/20 ml, in an assembly allowing azeotropic distillation to be conducted, preferably equipped with a Dean-Stark apparatus;
b) heating the mixture at a temperature of between 80 and 100° C., preferably at reflux of the benzene, for a period of between 4 and 48 h, preferably for 24 h;
c) allowing the temperature of the reaction mixture to return to ambient temperature;
d) drying the aqueous phase and then evaporating it to dryness;
e) optionally purifying the residue in accordance with customary methods, preferably by recrystallization.

The methods of deprotection of the carbonyl in position 17 of 3-O-acetyl-7α-hydroxy-DHEA protected in position 17 can be carried out in accordance with methods conventionally used in organic synthesis and well known to the person skilled in the art, such as, for example, those described in *Protective Groups in Organic Synthesis*, T. W. Greene, P. G. M. Wuts (Wiley Interscience).

Thus according to the invention a first preferred embodiment of the deprotection of the carbonyl in position 17 of 3-O-acetyl-7α-hydroxy-DHEA protected in position 17 in acetal form, preferably in cyclic acetal form, according to step (v) can be carried out in accordance with a method described in *Steroids* 1996, 61, 453–460, which has been modified.

This method consists essentially in
a) dissolving 3-O-acetyl-7α-hydroxy-DHEA protected in position 17 in acetal form in a mixture comprising water and a water-miscible solvent, preferably acetone, preferably in a 1/1 ratio by volume;
b) adding para-toluenesulphonic acid (p-TsOH), preferably 1 equivalent;
c) stirring the solution for a period of between 4 and 48 h, preferably 24 h, at ambient temperature;
d) evaporating the water-miscible solvent under vacuum;
e) diluting the reaction mixture with an organic solvent, selected preferably from ethyl acetate, dichloromethane, chloroform and diethyl ether, advantageously ethyl acetate, then washing it a number of times with water;
f) drying the organic phase and then evaporating it to dryness;
g) optionally purifying the residue in accordance with customary methods, preferably by recrystallization.

According to the invention a second preferred embodiment of the deprotection of the carbonyl in position 17 of the 3-O-acetyl-7α-hydroxy-DHEA protected in position 17 in acetal form, preferably cyclic acetal form, according to step (v) can be carried out in accordance with a method described in *Steroids* 1996, 61, 453–460, which has been modified.

Thus according to this other preferred embodiment of the invention the carbonyl in position 17 of the 3-O-acetyl-7α-hydroxy-DHEA protected in position 17 in acetal form, preferably in cyclic acetal form, is deprotected by a method described in *Synth. Comm.* 1995, 25, 395–404, which has been modified.

This method consists essentially in
a) preparing a solution consisting of 3-O-acetyl-7α-hydroxy-DHEA protected in position 17 in acetal form, preferably in cyclic acetal form, corresponding advantageously to 1,3-dioxolane or to 1,3-dioxane, in an organic solvent selected from benzene, chloroform and dichloromethane, preferably chloroform;
b) adding copper sulphate adsorbed on silica in an amount of between 2 and 4 g, preferably 2.5 g, per mmol of 3-O-acetyl-7α-hydroxy-DHEA protected in position 17 in acetal form;

c) stirring the reaction mixture for a period of between 1 to 48 h, preferably between 2 and 20 h, advantageously 6 h at a temperature of between 20 and 80° C., preferably between 50 and 70° C., advantageously at 60° C.;
d) filtering off the silica and concentrating the mixture to dryness;
e) optionally purifying the residue in accordance with customary methods, preferably by recrystallization.

The invention is illustrated in more detail in the following examples, which describe the various steps of the process in accordance with the invention.

EXAMPLE 1

Synthesis of 3-O-acetyl-7-oxo-DHEA of Formula (3)

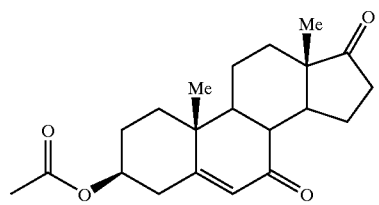

Method 1

A solution of 10 g of 3-O-acetyl-DHEA in 200 ml of acetonitrile is prepared. 60 mg of CuI are added under an inert atmosphere. The solution is cooled to between 5 and 10° C. and 19.6 ml of 80% t-BuOOH are added dropwise. At the end of the addition the temperature of the reaction mixture is allowed to rise to room temperature and it is stirred for 2 h and then heated at 50° C. for 20 h. The reaction mixture is subsequently cooled and is poured into 300 g of 10% sodium bicarbonate ($NaHCO_3$) solution. The mixture is extracted 3 times with diethyl ether and then the organic solution is washed with saturated $NaHCO_3$ solution and then with saturated sodium chloride (NaCl) solution. Drying and evaporation to dryness give the crude product in solid form. The residue is recrystallized from an acetone/hexane mixture.

Melting point: 190–192° C.;

yield: 91%;

$[\alpha]_d = -76°$ (methanol);

$^1H$ NMR and mass spectrometry are in agreement.

Method 2

A solution is prepared consisting of a mixture of 6.5 ml of acetic anhydride ($Ac_2O$), 23 ml of acetic acid (AcOH), 1.7 g of sodium acetate (NaOAc) and 2 g of 3-O-acetyl-DHEA. This system is stirred and the reaction mixture is heated to between 56 and 58° C. Subsequently 2 g of chromium trioxide ($CrO_3$) are added over 30 minutes, while keeping the temperature constant at between 56–58° C. The solution is stirred at this temperature for 1 h after the end of the addition, then cooled and added slowly (while stirring) to a solution of 600 ml of ice-water. The precipitate is filtered off and washed with water until it no longer has a green colour. It is dried under vacuum with diphosphorus pentoxide ($P_2O_5$) and recrystallized from methanol to give the product of formula (3) in solid form.

Melting point: 191–192° C.;

yield: 50–70%.

EXAMPLE 2

Synthesis of 3-O-acetyl-7α-OH-DHEA of Formula (4)

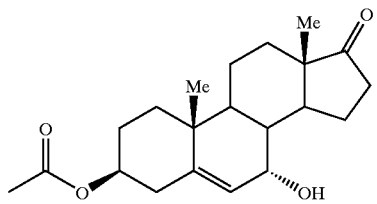

(4)

A solution of 300 mg of 3-O-acetyl-7-oxo-DHEA in 20 ml of anhydrous THF is prepared and is cooled to −78° C. 0.78 ml of L-Selectride®, sold by Aldrich (1 M in THF), is added dropwise under an inert atmosphere. The solution is stirred at −78° C. for 5 h. The reaction mixture is taken to 0° C. and 0.9 ml of NaOH solution (6 M) is added, followed by 0.9 ml of $H_2O_2$ (30%), and the mixture is stirred at ambient temperature for 30 minutes. It is diluted in 120 ml of diethyl ether. After a number of aqueous acid (5% citric acid), basic (saturated $KHCO_3$) and neutral washes, the organic solution is dried and then evaporated to dryness. The residue comprises 3-O-acetyl-7α-OH-DHEA (diastereoisomer obtained selectively) and approximately 10% of the product reduced in positions 7 and 17. The 7β-OH diastereoisomer was not identified in the mixture.

The residue is purified by chromatography to give 3-O-acetyl-7α-OH-DHEA in solid form.

Yield=70%;

$^1$H NMR and mass spectrometry are in agreement.

EXAMPLE 3

Synthesis of 7α-OH-DHEA of Formula (1)

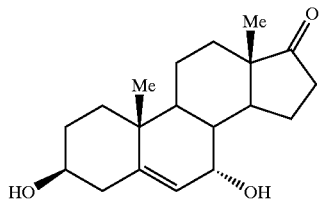

(1)

A solution of 3-O-acetyl-7α-OH-DHEA in methanol is prepared. 1 molar equivalent of sodium methoxide (NaOMe) is added and the mixture is stirred for a period of between 3 to 12 h. The methanol is evaporated, and the mixture is diluted with water and extracted with dichloromethane. The organic solution is dried then evaporated to dryness. The residue is purified by chromatography to give 7α-OH-DHEA in solid form.

Yield: 70%;

$[α]_d$=−66° (methanol);

melting point: 172–173° C.;

$^1$H NMR and mass spectrometry are in agreement.

EXAMPLE 4

Synthesis of 3-O-acetyl-17,17-ethylenedioxy-DHEA

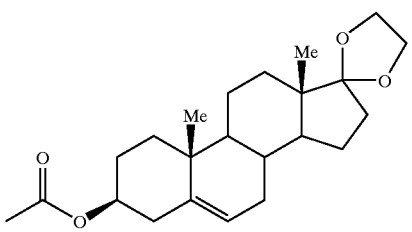

A solution of 1 mmol of 3-O-acetyl-DHEA in 3 ml of ethylene glycol and 2 ml of ethyl orthoformate is prepared. A catalytic amount of p-TsOH is added and the mixture is stirred at 40° C. for 3 h. It is cooled to ambient temperature and 10% $NaHCO_3$ solution is added. The mixture is extracted 3 times with dichloromethane and then the organic solution is washed with saturated NaCl solution. Drying and evaporation to dryness give the crude product in solid form. The residue is purified on silica gel (EtOAc/hexane, 17/83).

Yield: 77%;

melting point=135–137° C. (MeOH).

EXAMPLE 5

Synthesis of 3-O-acetyl-7-oxo-17,17-ethylenedioxy-DHEA

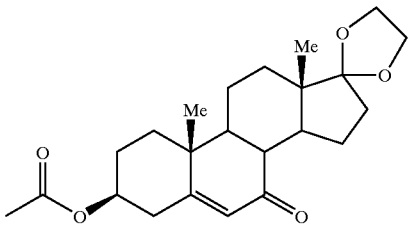

A solution of 374 mg of 3-O-acetyl-17,17-ethylenedioxy-DHEA in 3.5 ml of acetone and 3.5 ml of heptane is prepared. 2 ml of t-butyl hydroperoxide (70% in water) are added and the mixture is stirred at ambient temperature for 15 minutes, after which $NaIO_4$ (650 mg), water (0.9 ml) and sodium bicarbonate (55 mg) are added. This solution is subsequently stirred at ambient temperature for 14 h. The reaction mixture is diluted with ethyl acetate (10 ml) and washed with water, then 2 times with aqueous 15% sodium sulphate solution, then with water. Evaporation of the solvent gives the crude product in solid form, which is recrystallized from methanol.

Yield: 67%;

melting point: 182–183° C. (MeOH).

EXAMPLE 6
Synthesis of 3-O-acetyl-7α-hydroxy-17,17-ethylenedioxy-DHEA

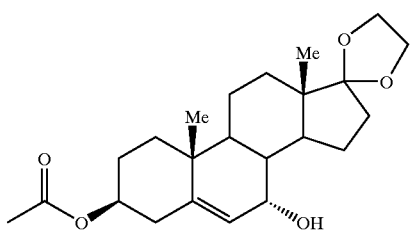

A solution of 800 mg of 3-O-acetyl-7-oxo-17,17-ethylenedioxy-DHEA in 20 ml of anhydrous THF is prepared and is cooled to −78° C. 2 ml of L-Selectride® (1 M in THF) are added dropwise under an inert atmosphere. The solution is stirred at −78° C. for 5 h. The reaction mixture is brought to 0° C. and 0.9 ml of NaOH solution (6 M) is added, followed by 2.25 ml of $H_2O_2$ (30%), and the mixture is stirred at ambient temperature for 30 minutes. It is diluted in 120 ml of diethyl ether. After a number of acid (5% citric acid), basic (saturated $KHCO_3$) and neutral washes, the organic solution is dried and then evaporated to dryness. The residue obtained, in which the 7β-hydroxy diastereoisomer was not identified, is purified by chromatography to give 3-O-acetyl-7α-hydroxy-17,17-ethylenedioxy-DHEA in solid form, which is purified on silica gel (EtOAc/hexane: 35/65).

Yield=75%;
melting point: 170–171° C.

EXAMPLE 7
Synthesis of 3-O-acetyl-7α-OH-DHEA of Formula (4)

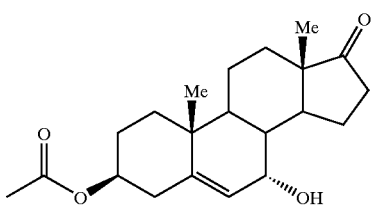

(4)

A solution of 1 mmol of 3-O-acetyl-7α-hydroxy-17,17-ethylenedioxy-DHEA in an acetone/water mixture (in a 1/1 ratio by volume) is prepared and p-TsOH (1 equivalent) is added. The solution is stirred at ambient temperature for 24 h. The acetone is then evaporated under vacuum. The reaction mixture is diluted with ethyl acetate and then washed a number of times with water. The organic phase is dried and then evaporated to dryness. The residue is purified by chromatography and recrystallized.

Yield: 95%;
melting point: 168–169° C. (acetone/hexane).

FIGURE 1

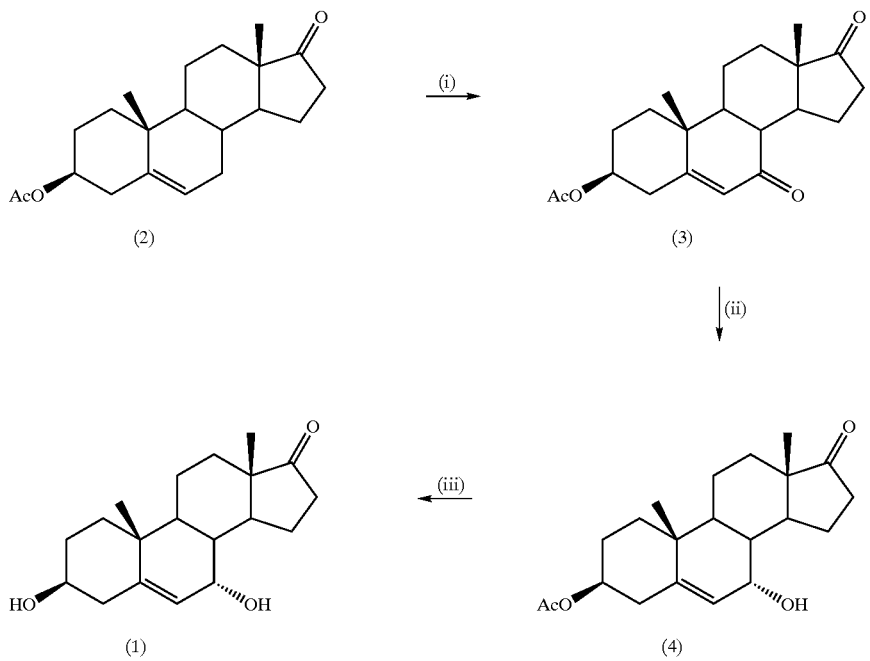

3-step process for synthesizing 7α-OH-DHEA (i) Oxidation in allyl position
(ii) Regioselective and siastereoselective reduction with L-Selectride[R]
(iii) Transesterification reaction

What is claimed is:

1. A method for preparing 7alpha-hydroxy-dehydroepiandrosterone of formula (1):

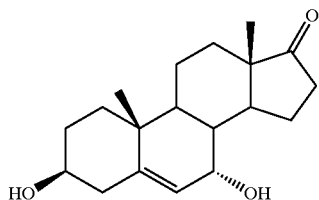

from 3-O-acetyl-7α-OH-DHEA, comprising a step (ii) in which 3-O-acetyl-7α-OH-DHEA is transesterified by contact with an alkali metal alkoxide in an alcoholic solvent, wherein step (iii) is preceded by a step (ii) comprising a regioselective and diastereoselective reduction of 3-O-acetyl-7-oxo-DHEA in the presence of lithium tri-sec-butylborohydride as a reducing agent, and wherein step (ii) is preceded by a step (i) comprising oxidizing 3-O-acetyl-DHEA in the allyl position.

2. A method according to claim 1, wherein step (iii) comprises the following steps:
   a) dissolving 3-O-acetyl-7α-OH-DHEA in an alcoholic solvent to form a reaction mixture,
   b) adding between 1 and 3 equivalents of an alkali metal alkoxide to the reaction mixture,
   c) stirring the reaction mixture for a period of between 0.5 and 12 h,
   d) evaporating the alcoholic solvent, thereby forming a mixture, diluting the mixture with water and extracting the diluted mixture with a solvent selected from the group consisting of dichloromethane, ethyl acetate, chloroform, diethyl ether, and mixtures thereof, thereby forming an organic phase,
   e) drying the organic phase and evaporating the organic phase to dryness, thereby forming a residue, and
   f) optionally purifying the residue.

3. The method according to claim 2, wherein
   in step a) the alcoholic solvent is selected from the group consisting of ethanol, methanol, tert-butanol, and mixtures thereof;
   in step b) between 1 and 1.5 equivalents, inclusive, of alkali metal alkoxide are added;
   in step c) the reaction mixture is stirred for a period of between 1 h and 5 h; and
   in step d) the solvent is dichloromethane.

4. The method according to claim 2, wherein in step b) the alkoxide is selected from the group consisting of ethoxide, tert-butoxide, methoxide, and mixtures thereof.

5. The method according to claim 2, wherein in step b) the alkali metal is selected from the group consisting of lithium, sodium, potassium, and mixtures thereof.

6. The method according to claim 1, wherein step (ii) comprises the following steps:
   a) dissolving 3-O-acetyl-7-oxo-DHEA in an anhydrous organic polar solvent to form a solution,
   b) cooling the solution to a temperature of between −90 and −10° C.,
   c) adding to the solution, under an inert atmosphere, between 0.9 and 1.1 equivalents of lithium tri-sec-butylborohydride,
   d) stirring the solution at a temperature of between −90 and −10° C. for a period of between 1 and 10 h,
   e) adjusting the temperature of the solution to between −10 and 10° C.,
   f) adding aqueous NaOH solution and aqueous $H_2O_2$ solution to the solution and stirring at ambient temperature,
   g) diluting the solution with an organic polar solvent,
   h) washing the diluted solution a plurality of times with at least one aqueous acidic solution, at least one aqueous basic solution and at least one aqueous neutral solution, thereby providing an organic phase,
   i) drying the organic phase and then evaporating it to dryness to form a residue, and
   j) optionally purifying the residue.

7. The method according to claim 6, wherein
   in step a) the anhydrous organic solvent is selected from the group consisting of tetrahydrofuran (THF), benzene, diethyl ether, and mixtures thereof;
   in step b) the solution is cooled to a temperature of −78° C.;
   in step c) between 0.95 and 1.05 equivalents of lithium tri-sec-butylborohydride are added;
   in step d) the solution is stirred at a temperature of between −80 and −60° C. for a period of between 1 and 10 h;
   in step e) the temperature of the reaction mixture is adjusted to 0° C.;
   in step g) the organic polar solvent is selected from the group consisting of diethyl ether, ethyl acetate, chloroform, dichloromethane, and mixtures thereof; and
   in step h) the diluted solution is washed a plurality of times with at least one aqueous 5% citric acid solution, at least one basic saturated aqueous $KHCO_3$ solution and at least one aqueous neutral solution.

8. The method according to claim 1, wherein step (i) comprises the steps of
   a) dissolving 3-O-acetyl-DHEA m an organic solvent or a mixture of organic solvents to form a reaction mixture,
   b) adding between 0.005 and 0.1 equivalent of copper to the reaction mixture,
   c) cooling the reaction mixture to a temperature of between −10 and 10° C.,
   d) adding between 5 and 10 equivalents of organic or inorganic peroxide to the reaction mixture,
   e) allowing the temperature of the reaction mixture to return to ambient temperature and stirring it for a period of between 0.5 and 4 h,
   f) heating the reaction mixture at a temperature of between 40 and 80° C. for a period of between 4 and 72 h,
   g) cooling the reaction mixture and adding it to an aqueous alkaline solution,
   h) extracting the aqueous phase with an organic solvent to form an aqueous phase and one or more organic phases,
   i) washing the organic phases with an aqueous alkaline solution and then optionally with a saturated aqueous NaCl solution,
   j) drying the organic phases and evaporating them to dryness under vacuum to form a residue, and
   k) optionally purifying the residue.

9. A method according to claim 8, wherein
   in step a) the organic solvent is selected from the group consisting of acetonitrile, cyclohexane, benzene, methanol, ethanol, tert-butanol, and mixtures thereof;

in step b) 0.01 equivalent of copper is added;

in step c) the reaction mixture is cooled to a temperature of between 5 and 10° C.;

in step d) 6 equivalents of organic or inorganic peroxide are added;

in step e) the reaction mixture is allowed to return to ambient temperature and is stirred for 2 h;

in step f) the reaction mixture is heated at a temperature of between 50 and 70° C.; for a period of between 16 and 24 h;

in step g) the aqueous alkaline solution is a 10% $NaHCO_3$ solution;

in step h) the organic solvent is selected from the group consisting of diethyl ether, ethyl acetate, chloroform, dichloromethane, and mixtures thereof, and in step i) the aqueous alkaline solution is a saturated $NaHCO_3$ solution.

10. The method according to claim 9, wherein in step b) the copper is a copper salt selected from the group consisting of CuI, CuBr, CuCl, $CuCl_2$, and mixtures thereof.

11. The method according to claim 8, wherein in step d) the peroxide is an alkyl hydroperoxide.

12. The method according to claim 1, wherein step (i) comprises the steps of a) preparing a reaction mixture consisting of acid anhydride, acetic acid, sodium acetate and 3-O-acetyl-DHEA, b) subjecting the reaction mixture to stirring and heating the reaction mixture to a temperature of between 40 and 60° C., c) adding between 1 and 10 equivalents of an oxide to the reaction mixture, d) maintaining the reaction mixture under stirring for a period of between 0.5 and 4 h at a temperature of between 40 and 60° C., e) cooling the reaction mixture and adding it to a solution consisting of water and ice, f) filtering off the resultant precipitate and washing it a plurality of times with water, and g) drying the precipitate and optionally purifying it.

13. The method according to claim 12, wherein in step b) the reaction mixture is heated to a temperature of between 56 and 58° C.;

in step c) between 2 and 6 equivalents of oxide are added;

in step d), the reaction mixture is maintained under stirring for a period of 1 h at a temperature of between 56 and 58° C.

14. The method according to claim 12, wherein in step c) the oxide is an oxide selected from the group consisting of an oxide of chromium, an oxide of manganese, an oxide of selenium, an oxide of magnesium, and mixtures thereof.

15. The method according to claim 1, wherein step (i) comprises the steps of a) dissolving 3-O-DHEA in an organic solvent or a mixture of organic solvents to form a solution, b) adding between 10 and 15 equivalents of an alkyl hydroperoxide to the solution to form a reaction mixture, c) stirring the reaction mixture at ambient temperature and adding between 1 and 5 equivalents of an alkali metal periodate, d) adding water in an amount sufficient to allow complete solubilization of the periodate in the reaction mixture, e) adding between 1 and 5 equivalents of organic bases or of weak inorganic bases to the reaction mixture, f) stirring the reaction mixture at ambient temperature for a period of between 8 and 48 h, g) diluting the reaction mixture with a second organic solvent, h) washing the reaction mixture a plurality of times with aqueous sodium sulphate solution and then with water, i) drying the organic phase of the reaction mixture and then evaporating the organic phase to dryness to form a residue, and j) optionally purifying the residue.

16. The method according to claim 15, wherein in step a) the organic solvent(s) is or are selected from the group consisting of acetone, heptane, acetonitrile, tert-butanol, pyridine, petroleum ether, hexane, isooctane, cyclohexane, and mixtures thereof;

in step b) the alkyl hydroperoxide is t-butyl hydroperoxide;

in step c) 3 equivalents of an alkali metal periodate are added;

in step d) between 20 and 30% of water by volume is added;

in step e) 3 equivalents of organic bases or of weak inorganic bases are added;

in step f) the reaction mixture is stirred at ambient temperature for a period of 14 h; and in step g) the second organic solvent is selected from the group consisting of ethyl acetate, dichloromethane, chloroform, diethyl ether, and mixtures thereof.

17. The method according to claim 15, wherein in step a) 3-O-acetyl-DHEA is dissolved in an organic solvent mixture consisting of acetone and heptane.

18. The method according to claim 17, wherein in step e) sodium bicarbonate is added.

19. The method of claim 1, further comprising the following additional steps:

(iv) protecting the carbonyl in position 17 of 3-O-acetyl-DHEA before step (i); and (v) deprotecting the carbonyl in position 17 of the oxidized 3-O-acetyl-DHEA obtained after step (ii), said deprotecting taking place before step (iii).

20. The method according to claim 19, wherein in step (iv) said protecting comprises forming a protecting group selected from the group consisting of a cyclic or non-cyclic acetal group, a cyclic or non-cyclic dithioacetal group, a monothicacetal group, an O-substituted cyanohydrin group, a substituted hydrazone group or an imine, an enamine, an imidazolidine and a benzothiazole group.

21. The method according to claim 20, wherein the carbonyl in position 17 of 3-O-acetyl-DHEA is protected in the form of a protecting group selected from the group consisting of a cyclic or non-cyclic acetal, cyclic or non-cyclic dithioacetal, imine, enamine and imidazolidine group.

22. The method according to claim 19, wherein the carbonyl in position 17 of 3-O-acetyl-DHEA is protected in the form of a cyclic acetal corresponding to 1,3-dioxolane or 1,3-dioxane.

23. The method according to claim 19, wherein said protecting is an acetalization reaction comprising the steps of a) preparing a reaction mixture comprising 3-O-acetyl-DHEA, a diol and a desiccant, b) adding a catalytic amount of proton to the reaction mixture, c) stirring the reaction mixture at a temperature of between 30 and 60° C. for a period of between 1 and 8 h, d) adjusting the temperature of the reaction mixture to ambient temperature, e) adding an aqueous $NaHCO_3$ solution to the reaction mixture, f) extracting the reaction mixture with a solvent selected from the group consisting of dichloromethane, chloroform, ethyl acetate, and diethyl ether, and mixtures thereof to form an organic phase, g) drying the organic phase and evaporating it to dryness to form a residue, h) optionally purifying the residue.

24. The method according to claim 23, Wherein in step a) the diol is ethylene glycol and the desiccant is selected from the group consisting of molecular sieve and ethyl orthoformate;

in step b) the source of the catalytic amount of proton is para-toluenesulphonic acid or ion exchange resins;

in step c) the mixture is stirred at a temperature of 40° C. for 3 h;

in step f) the solvent is dichloromethane.

25. The method according to claim 23, wherein in step a) the 3-O-acetyl-DHEA, the diol and the desiccant are present in the solution, respectively, in a ratio of 1 mmol/3 mL/2 nil.

26. The method according to claim 19, wherein said protecting is an acetalization reaction comprising the steps of a) bringing to reflux a reaction mixture consisting of 3-O-acetyl-DHEA, ethylene glycol and para-toluenesulphonic acid (p-TsOH) in solution in benzene, in an assembly allowing an azeotropic distillation to be carried out, b) heating the solution at a temperature of between 80 and 100° C. for a period of between 4 and 48 h, c) allowing the reaction mixture to return to ambient temperature, d) drying an organic phase of the reaction mixture and evaporating the organic phase to dryness to form a residue;

e) optionally purifying the residue.

27. The method according to claim 26, wherein in step a) 3-O-acetyl-DHEA, ethylene glycol, para-toluenesulphonic acid and benzene are present in the reaction mixture in a ratio, respectively, of 1 mmol/5 ml/0.1 mmol 20 ml and the assembly allowing an azeotropic distillation to be carried out is equipped with a Dean-Stark apparatus;

in step b) the solution is heated at the reflux of the benzene for 24 h.

28. The method according to claim 19, wherein said deprotecting of step (v) is a deacetalization reaction.

29. The method according to claim 20, wherein said deprotecting comprises the steps of a) dissolving 3-O-acetyl-7α-DHEA protected in position 17 in acetal form in a reaction mixture comprising water and a water-miscible solvent, b) adding para-toluenesulphonic acid to the reaction mixture, c) stirring the reaction mixture at ambient temperature for a period of between 4 and 48 h, d) evaporating the water-miscible solvent under vacuum, e) diluting the reaction mixture with an organic solvent and then washing the reaction mixture a plurality of times with water, f) drying an organic phase of the reaction mixture and evaporating the organic phase to dryness to form a residue, g) optionally purifying the residue.

30. The method according to claim 29, wherein in step a) the water and the water-miscible solvent are in a 1/1 ratio by volume;

in step b) 1 equivalent of para-toluenesulphonic acid is added;

in step c) the reaction mixture is stirred for 24 h;

in step e) the organic solvent is selected from the group consisting of ethyl acetate, dichloromethane, chloroform, diethyl ether, and mixtures thereof.

31. The method according to claim 28, wherein said deprotecting comprises the steps of a) preparing a reaction mixture consisting of 3-O-acetyl-DHEA protected in position 17 in acetal form in an organic solvent, b) adding copper sulphate adsorbed on silica in an amount of between 2 and 4 g per mmol of 3-O-acetyl-7α-hydroxy-DHEA protected in position 17 in acetal form to the reaction mixture, c) stirring the reaction mixture at a temperature of between 20 and 80° C. for a period of between 1 to 48 h, d) filtering off the silica and concentrating the reaction mixture to dryness to form a residue, e) optionally purifying the residue.

32. The method according to claim 31, wherein in step a) the organic solvent is selected from the group consisting of benzene, chloroform, dichloromethane, and mixtures thereof;

in step b) the copper sulphate adsorbed on silica is added in an amount equal to 2.5 g per mmol of 3-O-acetyl-7α-DHEA protected in position 17 in acetal form;

in step c) the reaction mixture is stirred for a period of between 2 and 20 h and at a temperature of between 50 and 70° C.

33. The method of claim 3, wherein the amount of alkali metal alkoxide of step b) is 1 equivalent.

34. The method of claim 3, wherein in step c) the reaction mixture is stirred for approximately 2 h.

35. The method of claim 7, wherein in step c), 1 equivalent of lithium tri-sec-butylborohydride is added.

36. The method of claim 7, wherein in step d) the solution is stirred at approximately −78° C. for a period of 5 h.

37. The method of claim 9, wherein in step b) copper is added in the form of a salt.

38. The method of claim 9, wherein in step d) an organic peroxide is added.

39. The method of claim 11, wherein the alkyl hydroperoxide is t-butyl hydroperoxide.

40. The method of claim wherein 3.5 equivalents of oxide are added.

41. The method of claim 14, wherein the oxide is chromium trioxide ($Cr_{O3}$).

42. The method of claim 15, wherein in step d) between 10% and 50% by volume of water is added.

43. The method of claim 16, wherein in step c) the alkali metal periodate is sodium periodate (NaIO).

44. The method of claim 16, wherein pyridine is added.

45. The method of claim 16, wherein a base selected from the group consisting of alkali carbonates and bicarbonates is added.

46. The method of claim 17, wherein the acetone and heptane are present in a ratio of 1/1.

47. The method of claim 21, wherein said protecting group is a cyclic acetal group.

48. The method of claim 30, wherein the water-miscible solvent is acetone.

49. The method of claim 32, wherein in step c) the reaction mixture is stirred for approximately 6 hours at a temperature of approximately 60° C.

50. The method of claim 1, wherein the alcoholic solvent comprises the corresponding alcohol of the alkali metal alkoxide.

51. The method of claim 1, wherein the alcoholic solvent comprises an alcohol selected from the group consisting of ethanol, methanol, tert-butanol, and mixtures thereof.

52. The method of claim 1, wherein between 1 and 3 equivalents of the alkali metal alkoxide are added to the reaction mixture.

53. The method according to claim 1, wherein the alkoxide is selected from the group consisting of ethoxide, tert-butoxide, methoxide, and mixtures thereof.

54. The method according to claim 1, wherein the alkali metal is selected from the group consisting of lithium, sodium, potassium, and mixtures thereof.

55. The method according to claim 1, wherein the alkali metal alkoxide is sodium methoxide.

56. The method according to claim 51, wherein the alcohol is methanol.

57. The method according to claim 50, wherein the alcohol is methanol.

* * * * *

UNITED STATES PATENT AND TRADEMARK OFFICE
CERTIFICATE OF CORRECTION

PATENT NO. : 6,930,192 B2
DATED : August 16, 2005
INVENTOR(S) : Maria Dalko et al.

It is certified that error appears in the above-identified patent and that said Letters Patent is hereby corrected as shown below:

Column 13,
Line 15, change "(ii)" to -- (iii) --;
Line 35, "dichioromethane" should read -- dichloromethane --.

Column 14,
Line 31, "dichioromethane" should read -- dichloromethane --;
Line 39, "m an organic" should read -- in an organic --.

Column 15,
Line 15, "dichioromethane" should read -- dichloromethane --.

Column 17,
Line 10, "dichioromethane" should read -- dichloromethane --;
Line 16, "Wherein" should read -- wherein --;
Line 25, "dichioromethane" should read -- dichloromethane --;
Line 28, "mL/2 nil" should read -- ml/2 ml --;
Line 50, "20 ml" should read -- /20 ml --;
Line 59, "3-O-acetyl-7α-DHEA" should read -- 3-O-acetyl-7α-hydroxy-DHEA --.

Column 18,
Line 17, "dichioromethane" should read -- dichloromethane --;
Line 21, "3-O-acetyl-DHEA" should read -- 3-O-acetyl-7α-hydroxy-DHEA --;
Line 41, "7α-DHEA" should read -- 7α-hydroxy-DHEA --;
Line 59, "of claim wherein" should read -- of claim 13 wherein --.

Signed and Sealed this

Twenty-seventh Day of December, 2005

JON W. DUDAS
*Director of the United States Patent and Trademark Office*